US 8,008,541 B2

(12) United States Patent
Anstrom et al.

(10) Patent No.: US 8,008,541 B2
(45) Date of Patent: Aug. 30, 2011

(54) PHENOTYPIC SCREEN FOR PLANTS

(75) Inventors: Donald Anstrom, Pawcatuck, CT (US); Paul Chomet, Mystic, CT (US); Adrian Lund, Halstead, KS (US)

(73) Assignee: Monsanto Technology LLC, St. Louis, MO (US)

( * ) Notice: Subject to any disclaimer, the term of this patent is extended or adjusted under 35 U.S.C. 154(b) by 197 days.

(21) Appl. No.: 11/848,357

(22) Filed: Aug. 31, 2007

(65) Prior Publication Data

US 2008/0057511 A1    Mar. 6, 2008

Related U.S. Application Data

(60) Provisional application No. 60/841,383, filed on Aug. 31, 2006.

(51) Int. Cl.
*A01H 1/04*    (2006.01)
*C12N 15/82*   (2006.01)

(52) U.S. Cl. ........ 800/278; 800/289; 800/279; 800/300; 435/6; 435/91.2

(58) Field of Classification Search .................. 800/276, 800/278, 287, 289, 293, 294, 279, 300; 435/6, 435/91.2
See application file for complete search history.

(56) References Cited

U.S. PATENT DOCUMENTS

| | | |
|---|---|---|
| 5,015,580 A | 5/1991 | Christou et al. |
| 5,538,880 A | 7/1996 | Lundquist et al. |
| 5,550,318 A | 8/1996 | Adams et al. |
| 5,591,616 A | 1/1997 | Hiei et al. |
| 5,633,435 A | 5/1997 | Barry et al. |
| 5,635,055 A | 6/1997 | Sweet et al. |
| 5,780,708 A | 7/1998 | Lundquist et al. |
| 5,824,877 A | 10/1998 | Hinchee et al. |
| 5,914,451 A | 6/1999 | Martinell et al. |
| 5,981,840 A | 11/1999 | Zhao et al. |
| 6,118,047 A | 9/2000 | Anderson et al. |
| 6,160,208 A | 12/2000 | Lundquist et al. |
| 6,384,301 B1 | 5/2002 | Martinell et al. |
| 6,399,861 B1 | 6/2002 | Anderson et al. |
| 6,403,865 B1 | 6/2002 | Koziel et al. |
| 2005/0097640 A1* | 5/2005 | Fernandes .................... 800/289 |

OTHER PUBLICATIONS

Koiwa et al. 2006. J. Experimental Botany 57(5): 1119-1128, advance access publication Mar. 2, 2006.*
Holbrook et al, 1995, Crop Sci. 35 1700-1702.

* cited by examiner

*Primary Examiner* — David T Fox
*Assistant Examiner* — Keith O. Robinson
(74) *Attorney, Agent, or Firm* — James E. Davis

(57) ABSTRACT

The present invention is directed to a method of identifying plants with enhanced agronomic traits within a larger population of plants grown from a randomly planted set of seeds.

10 Claims, No Drawings

PHENOTYPIC SCREEN FOR PLANTS

CROSS-REFERENCE TO RELATED APPLICATIONS

This application claims the benefit of priority of prior filed U.S. Application Ser. No. 60/841,383 filed Aug. 31, 2006, which is herein incorporated by reference in its entirety.

FIELD OF THE INVENTION

Disclosed herein are methods of identifying DNA that confers a trait within a population of plants.

BACKGROUND OF THE INVENTION

Recent advances in genetic engineering and plant breeding have provided the prerequisite tools to transfer genes and regions of a genome in plants to improve certain phenotypes in plants. It is possible to produce plants with unique physiological and biochemical traits and characteristics of high agronomic importance. Traits that play an essential role in plant growth and development, as well as, crop yield, crop quality, and composition are desirable targets for crop plant improvement.

Evaluation of a limited number of modified plants is often done in a manner that compares a single modified event to a nonmodified control. In these evaluations, each event is well tracked and known throughout the evaluation. The goal of initial evaluations is often to identify if the gene or the genetic region has a biological effect for a trait of interest. Extensive evaluations of a large number of events can be limited because of the size of the field and the difficulty in environmental control of the fields under evaluation. Also extensive measurements of each replicate of a modified event often limits the total number of evaluations that can be done due to the large effort needed to consistently take such measurements.

Improvement of plants by plant breeding and other means is the hallmark of agricultural productivity in present times. A major part of this involves evaluation of large number of plants in a systematic manner. For these evaluations, plant populations or individual plants are evaluated by comparison with control plants or plant populations. Methods of evaluation are difficult and expensive because of many factors, for example space requirements imposed by nonrandom and systematic comparisons resulting in a large population of plants in a given test.

There are several methods of altering plants to select plants with improved or enhanced agronomic traits. One such method is by transforming a plant with one or more DNA molecules in a plant genome that is capable of producing a desired trait in the transformed plant compared to a non-transformed plant. Other methods of altering plants involve plant breeding where plants are crossed to produce progeny with different phenotypes to select desired plants. Plant breeding is sometimes assisted by one or more genetic markers or traits that serve especially to identify genes or traits linked with markers. Even in marker assisted plant breeding tracking of markers in a population of progeny results in exponential increment of cost imposed by tracking itself and space requirements.

SUMMARY OF THE INVENTION

We have developed a unique method to evaluate large populations of plants. This screening method allows for quick and efficient evaluation of such plants for one or more traits. The key to this method is the evaluation of a population of modified plants in a "forward genetics" screen rather than a "reverse genetics" investigation. In a forward genetics screen, the goal is to identify genes or genetic regions (or mutations) that produce a certain phenotype. Once plants showing this phenotype have been isolated, the gene or genetic region can be molecularly identified. This is in contrast to a reverse genetics screen which is the usual evaluation method for modification in plants.

More specifically this invention provides a novel method of screening a genetically diverse plant population to identify one or more plant lines with improved agronomic traits. Such a method allows identifying genes that confer enhanced traits within a population of plants. In this method a known number of seeds from different plant lines with unique characteristics, i.e. genetic variability, are collected and planted to produce a random plant population. Such genetic variability can be due to one or more transgenes; e.g. the plant lines can be transgenic crop plants events. Alternatively, genetic variability can be due to one or more genetic markers. For example, a minimum of two seeds from each transgenic event in a population can be used in a mixed pool of seeds, but a higher number of seeds from each event provides a better chance of finding events with a desired trait. Care should be taken to have the same number of seeds from each plant line, e.g. transgenic event, in pools to simplify the analysis. In one aspect of the invention the pools of seeds is mixed prior to planting to obtain a seed mixture having the same number of seeds from each plant line.

A random plant population can be planted in field, green house or growth chamber where the plants are grown from a mixed pool of seeds, exposed to a common environment and screened to identify individual plants with improved agronomic traits. The plants are evaluated to identify a sample population of plants exhibiting an enhanced trait; and the genotype of plants exhibiting an enhanced trait is determined. In one aspect of the invention screening of plants involves calculating the expected frequency of a plant line in the random mixture and measuring the observed frequency of plants with improved agronomic traits after exposure to a common environmental treatment and selection for improved traits. More specifically, screening of plants is further refined by determining the expected frequency of randomly selecting a plant line within the population of plants; determining the observed frequency of each plant line in the sample population of plants exhibiting an enhanced trait; applying a statistical test to compare the observed frequency with the expected frequency for plants from each plant line to assign significance for each comparison; and identifying plant lines where the observed frequency is greater than the expected frequency to select plant lines with an enhanced trait. This treatment allows for improved agronomic traits to be revealed among the screened plants. The observed frequency is then compared with the expected frequency to assign significance and identify select plant lines with desired traits.

In one aspect, genetic variability of a plant population is due to a naturally occurring variability in its genome characterized by differences in genetic markers which are associated to or reveal the genetic variation.

In another aspect, genetic variability of a plant population is due to one or more transgenes artificially introduced into the plant genome. In other cases genetic variability in plant lines is created by causing a mutation, causing a recombination, or artificial breeding in parental lines used for creating plant lines.

Other aspects of the invention are crop plants that are screened using the disclosed methods and identified as having a desired trait.

The common environment can be capable of causing biotic stress, abiotic stress of be induced by application of one or more chemicals, e.g. an herbicide. Such biotic stress can be caused by plants, fungi, bacteria, viruses or animals such as insects or nematodes. Such abiotic stress can be caused by an excess or limitation of heat, minerals, acidity, water, salt, light or gases.

Agronomic traits of the invention include biotic stress tolerance such as pest and insect tolerance, chemical tolerance such as herbicide tolerance, abiotic stress tolerance such as water deficiency tolerance, improved and altered seed compositions, plant height, pod number, pod position on the plant, number of internodes, incidence of pod shatter, grain size, efficiency of nodulation and nitrogen fixation, efficiency of nutrient assimilation, resistance to biotic and abiotic stresses, carbon assimilation, plant architecture, resistance to lodging, percent seed germination, seedling vigor, and juvenile traits. Other traits embodied in the present method include efficiency of germination (including germination in stressed conditions), growth rate (including growth rate in stressed conditions), ear number, seed number per ear, seed size, composition of seed (starch, oil, protein) and characteristics of seed fill under normal and high density plantings.

DETAILED DESCRIPTION OF THE INVENTION

For transforming a plant with a desired DNA molecule, DNA that is capable of producing a functional protein or an antisense mRNA within a plant is cloned in a DNA construct also referred to as a vector. Two commonly used methods for transforming plants with such DNA constructs are *Agrobacterium*-mediated transformation and microprojectile bombardment. Microprojectile bombardment methods are illustrated in U.S. Pat. Nos. 5,015,580; 5,550,318; 5,538,880; 5,914,451; 6,160,208; 6,399,861 and 6,403,865, and *Agrobacterium*-mediated transformation is described in U.S. Pat. Nos. 5,635,055; 5,824,877; 5,591,616; 5,981,840 and 6,384, 301, all of which are incorporated herein by reference. For *Agrobacterium tumefaciens* based plant transformation systems, additional elements present on transformation constructs will include T-DNA left and right border sequences to facilitate incorporation of the recombinant DNA into the plant genome. In practice DNA is introduced into only a small percentage of target cells in any one experiment. Marker genes are used to provide an efficient system for identification of those cells that are stably transformed by receiving and integrating a transgenic DNA construct into their genomes. Preferred marker genes encode proteins that confer resistance to a selective agent, such as an antibiotic or herbicide. Potentially transformed cells are exposed to the selective agent. In the population of surviving cells, there will be those cells where, generally, the resistance-conferring gene has been integrated and expressed at sufficient levels to permit cell survival. Cells may be tested further to confirm stable integration of the exogenous DNA. Useful selectable marker genes include those conferring resistance to antibiotics. Examples of such selectable marker are illustrated in U.S. Pat. Nos. 5,550,318; 5,633,435; 5,780,708 and 6,118,047, all of which are incorporated herein by reference. Cells that survive exposure to the selective agent or cells that have been scored positive in a screening assay, may be cultured in regeneration media and allowed to mature into plants by well known methods in the art. Transformed plants can be tracked by a number of screening methods involving detection of DNA molecules introduced in the plant genome by plant transformation. Commonly used methods for tracking newly introduced DNA include: PCR, southern and northern blot analyses, which are well known in the art. Similar methods can also be used to track markers in plant breeding methods.

The term trait, sometimes referred to as phenotypic trait or phenotype, is an observable trait of an organism resulting from an interaction between the genotype of the organism and the environment. Traits that are important to agricultural plants are also referred as agronomic traits. A phenotypic trait can be observed by the naked eye or by any other means of evaluation known in the art, for example microscopy, biochemical analysis, etc. The trait selected for using the methods of the current invention can be any quantitative or qualitative phenotypic trait. In some embodiments the trait is resistance or tolerance to one or more chemicals including herbicidal chemicals. Herbicidal chemicals include glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides, glufosinate herbicides, auxin like herbicides, 3,6-Dichloro-2-methoxybenzoic acid, (2,4-dichlorophenoxy)acetic acid, 4-(2,4-dichlorophenoxy) butyric acid, 2-(2,4-dichlorophenoxy)propanoic acid, (2,4,5-trichlorophenoxy)acetic acid, 2-(2,4,5-Trichlorophenoxy) Propionic Acid, 2-(2,4-dichloro-3-methylphenoxy)-N-phenylpropanamide, (4-chloro-2-methylphenoxy)acetic acid, 4-(4-chloro-o-tolyloxy)butyric acid, 2-(4-chloro-2-methylphenoxy)propanoic acid, 3,6-dichloro-2-pyridinecarboxylic acid, 4-amino-3,5,6-trichloro-2-pyridinecarboxylic acid, (2,4,5-trichlorophenoxy)acetic acid, 4-amino-3,5-dichloro-6-fluoro-2-pyridyloxyacetic acid, 3-amino-2,5-dichlorobenzoic acid, 3,7-dichloro-8-quinolinecarboxylic acid, and 7-chloro-3-methyl-8-quinolinecarboxylic acid.

In some embodiments, the trait is selected from the group consisting of root lodging, stalk lodging, plant lodging, plant height, plant morphology, ear development, tassel development, plant weight, plant maturity, total plant or plant part dry matter, fruit and seed size, harvest moisture, husk length, stand count at harvest time in a unit area or per plot, crop yield, metabolite quality or content which include oil, protein, carbohydrate or any other plant metabolite, insect or nematode resistance or tolerance, viral, bacterial or fungal disease resistance or tolerance, abiotic stress resistance or tolerance as represented by resistance or tolerance to drought, heat, chilling, freezing, excessive moisture, salt or oxidative stress, food or feed content and value, physical appearance, male sterility, and the like. As those skilled in the art will readily recognize, the invention may be practiced using any combination of phenotypic traits that is imparted by one or more transgenes introduced by plant transformation or statistically associated with more than one genomic locus, such as a QTL or a combination of both.

Often effects of the environment mask those of the genotype, so the phenotype provides an imperfect measure of a plant's biological or genetic potential. Because of this, a modified plant population is exposed to a common environment for practicing the invention. According to the present invention the common environment will be capable of exposing a subset of plants with an enhanced desired trait within the population. For example, drought tolerant plants within a population can be identified by exposing the plant population to drought; herbicide tolerant plants within a population can be identified by exposing the plant population to a specific herbicide; insect tolerant plants within a population can be identified by exposing the plant population to a specific insect; nitrogen deficit tolerant plants within a population can be identified by exposing the plant population to a nitrogen deficit; and plants with enhanced yield within a population can be identified by measuring plant height at various time points, determining chlorophyll fluorescence (SPAD measurement) or harvesting from individual plants to determine yield, such as grain yield. The common environment in the present invention is not necessarily a uniform environment. In a useful embodiment, the plants are planted and evaluated in one continuous field planting. Randomization of the seeds for planting allows the plants to be evaluated in a blind study and reduces the impact of the variability of specific locations within a field.

Plants harboring transgenes or mutations in this screen are compared to their neighbors to identify improved traits, and the genes present in the selected plants identified by sequence analysis. In this manner genes conferring better performing plants are identified and further analyzed to determine if the effect is due to a transgene expression or random occurrence. This is done through the leveraging of repetition of a transgene where one can accurately assess a clear association between the gene and the phenotype. The statistic is calculated using chi-square method based on the gene frequency in the planted population and the total number of transgene events selected as having improved traits.

The present invention provides a method of identifying enhanced traits within a population of plant species. In preferred embodiment plant species can be a plant species that can produce a crop. According to present invention crop plants are plants that can be grown and harvested extensively for profit or subsistence. Any crop species can be used in this invention. The method of the invention is especially useful for hybrid crop plants such as corn.

Variations of the methods provided herein may also find application for identification of genes which impart improved properties to transgenic plants. For example, plants may be planted in a random distribution, but under planting conditions such that the genetic identity of each individual plant is known at planting. In this manner, the number of replicates needed to detect biologically significant differences among a plant population can be reduced, and plants compared with their neighboring plants to identify trait improved plants. The genes which impart improved phenotypes to the transgenic plants can then be identified without sequencing or other analysis based on the known location of the test plants.

The following example illustrates one aspect of the invention by describing the selection of transgenic corn hybrid plants having improved drought tolerance from a population of over 13,000 hybrid corn plants representing 663 transgenic events prepared by transformation using 186 unique constructs. Exactly 20 hybrid corn seeds for each of the transgenic events were randomized in a tumbler to create a pool of seeds. Multiple sets of an identical pool were prepared for planting at different locations.

Prior to planting, each field was prepared with pre-emergent herbicide and all necessary fertilizers, which were applied and incorporated into the soil by following recommended label rates and normal tillage practices. Corn insect pest were monitored and proactively controlled, as needed, through the use of insecticide by following label rates. Seeds of identical pools were planted at multiple test locations at a density of 32,000 plants/acre. Plants were evenly spaced in the field to ensure that environmental effects are similar for each plant in the field. The plot structure was conventional corn rows on 30" centers. Each row was planted with drip-tape to facilitate uniform water distribution of water to initiate germination. To generate water stress or drought conditions, the population stand was allowed to attain V8 stage of growth under normal watering conditions. At V8 stage, irrigation water was withheld until about 98% of the population exhibited extreme drought symptoms, e.g. very rolled leaves, poor internode expansion, light green leaves, reduced tassel emergence, little or no silk emergence, little or poor ear development. The duration of this water regime spanned the V8 leaf through the R2 reproductive stage.

To identify individual plants that show improved growth under stress conditions, at least two persons walk through the field at various times between the VT and R2 stages of plant development to allow for both identification and verification of drought tolerance. Plants that represented 1-2% of the population that best exhibited improved cumulative vegetative and reproductive characteristics, e.g. greenness, plant height/internode expansion, leaf flatness/wilting, ear development, silk development/vigor and tassel development/emergence were identified. Identified plants were tagged with an ID, photographed, and sampled for further analysis.

Leaf samples were taken from individual plants that had a positive growth response under water stress. Because the quality of the plant material is important for quality of molecular analysis, the youngest/freshest leaf material was collected for analysis. DNA was isolated from the tissue samples and used as template for amplification of the inserted transgenic DNA using commercially available sequencing kits producing sequence information that was compared to the known set of transgene coding region sequences used in the field study.

The null hypothesis is that the selection of plants is no better than selecting plants randomly. Chi square analysis was used to test the null hypothesis for each plant construct in the study. Since it was known how many plants for a given construct were planted in the field and how many plants were selected and sampled, we can calculate the expected frequency of randomly selecting a transgenic plant that contains a given construct. Sequence identification of the sampled plants allows us to calculate the observed frequency for a given construct in the sampled population. Chi square analysis indicates if the observed frequency for a construct was significantly different from random. If the frequency of identifying a particular construct is significantly higher than random (at $P \leqq 0.05$), it indicates that the null hypothesis (the selection of plants is no better than selecting plants randomly) is not true. This is suggestive that a given gene has improved plant growth under stress conditions.

For example, the construct identified as pMON67819 was represented in three transgenic events with 60 plants randomly planted in a field of 13260 plants (assuming 100% germination). Therefore 0.45% of the plants will have sequences from construct pMON67819. If 190 samples are collected, about 1 plant would be randomly sampled from pMON67819. If 3 of the 190 samples were identified to have pMON67819 sequences then chi square analysis will show that this sampling is not random at a probability of $p=0.023$. Therefore, we have systematically selected plants that grow better under these drought conditions and these plants contain the gene in pMON67819. The data presented in Table 1 demonstrates the use of this method to identify additional genes that contributed to improved plant growth under these stress conditions.

This screen enabled the characterization of about 180 genes in a single experiment. Of the individual events, 57 were found to be related to the 14 genes listed on above table. Fourteen different genes were identified and shown to confer stress tolerance when over-expressed in corn. These 14 genes are useful for generating crop lines that are more drought and stress tolerant and have increased yield stability.

TABLE 1

| Construct | ID | Gene Name | Events | Exp. Freq. | Obs. Freq. | Chi Test |
|---|---|---|---|---|---|---|
| pMON68392 | PHE0000457 | *Arabidopsis* Transcription Factor G 1543 | 14 | 4.08 | 8 | 0.052 |
| pMON78941 | PHE0001421 | Maize Glutamate Dehydrogenase | 5 | 1.46 | 4 | 0.035 |
| pMON68634 | PHE0000593 | Maize L5-Like | 5 | 1.46 | 4 | 0.035 |
| pMON73795 | PHE0000854 | Soy 14-3-3 22 | 3 | 0.87 | 3 | 0.023 |
| pMON79160 | PHE0001398 | Maize Ran Binding protein homolog | 3 | 0.87 | 3 | 0.023 |
| pMON68390 | PHE0000459 | Anabaena Sucrose Phosphate Phosphatase | 11 | 3.2 | 8 | 0.007 |
| pMON75451 | PHE0000540 | Maize Tubby 4 | 4 | 1.16 | 4 | 0.009 |
| pMON75335 | PHE0000862 | Maize 14-3-3 13 N-terminus | 2 | 0.58 | 3 | 0.002 |
| pMON75333 | PHE0000860 | Rice 14-3-3 15 N-terminus | 1 | 0.29 | 2 | 0.002 |
| pMON79672 | PHE0001423 | Maize Glutamate Decarboxylase | 1 | 0.29 | 2 | 0.002 |
| pMON67819 | PHE0000004 | Maize HAP3 Like Transcription Factor | 3 | 0.87 | 3 | 0.023 |
| pMON68862 | PHE0000093 | *Arabidopsis* Transcription Factor G 682 | 4 | 1.16 | 6 | 0 |
| pMON68606 | PHE0000658 | *Arabidopsis* Transcription Factor G 1496 | 2 | 0.58 | 4 | 0 |
| pMON68863 | PHE0000135 | Maize Putative Protein Phosphatase type 2C | 1 | 0.29 | 3 | 0 |

Table Legends:
Events: Total Number of transgenic plants containing a designated construct in the test,
Exp. Freq.: Expected Frequency of randomly selecting a transgenic plant that contains a given construct,
Obs. Freq.: Observed Frequency of identifying a transgenic plant that contains a given construct in a sample population selected as having improved plant growth, Repeated testing in subsequent seasons using the methods described herein demonstrates the ability to consistently identify transgenes which impart stress tolerance to transgenic plants under various planting densities and under varying stress conditions and varying severity of stress.

What is claimed is:

1. A method of identifying one or more transgenes that confer desired traits within a population of crop plants, the method comprising:
   a) preparing a seed mixture comprising seeds from a group of crop plant lines, the seed mixture comprising an equal number of seeds from each crop line; wherein each crop plant line comprises a unique transgenic event, said transgenic event comprising a genetic construct which comprises one or more transgenes;
   b) planting said seed mixture to produce a random plant population, wherein each seed in the mixture is planted;
   c) exposing said plant population to a common environment;
   d) evaluating the plants in said plant population to identify plants exhibiting one or more desired traits; and
   e) determining the presence of said one or more transgenes in said plants exhibiting said one or more desired traits.

2. The method of claim 1 wherein said method further comprises:
   f) determining the expected frequency of randomly selecting a plant line comprising a given construct within said population of plants;
   g) determining the observed frequency of each plant line comprising a given construct in the sample population of plants exhibiting one or more desired traits;
   h) applying a statistical test to compare the observed frequency with the expected frequency for plants from each plant line, to assess significance for each comparison; and
   i) identifying plant lines comprising a given construct where the observed frequency is greater than the expected frequency, to select plant lines comprising one or more transgenes which confer one or more desired traits.

3. The method of claim 1 wherein said seed mixture comprises at least two seeds from each plant line.

4. The method of claim 1 wherein said seed mixture is planted in a green house or growth chamber.

5. The method of claim 1 wherein said seed mixture is planted in a field.

6. The method of claim 1 wherein said environment is capable of causing biotic or abiotic stress in said crop plant.

7. The method of claim 1 wherein said environment is induced by application of one or more chemicals.

8. The method of claim 6 wherein said abiotic stress is caused by heat, minerals, acidity, water, light or gases.

9. The method of claim 6 wherein said biotic stress is caused by, plants, fungi, animals, or viruses.

10. The method of claim 7 wherein said one or more chemicals are selected from the group consisting of glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides, glufosinate herbicides, auxin like herbicides, 3,6-Dichloro-2-methoxybenzoic acid, (2,4-dichlorophenoxy)acetic acid, 4-(2,4-dichlorophenoxy)butyric acid, 2-(2,4-dichlorophenoxy)propanoic acid, (2,4,5-trichlorophenoxy)acetic acid, 2-(2,4,5-trichlorophenoxy)propanoic acid, 2-(2,4-dichloro-3-methylphenoxy)-N-phenylpropanamide, (4-chloro-2-methylphenoxy)acetic acid, 4-(4-chloro-o-tolyloxy)butyric acid, 2-(4-chloro-2-methylphenoxy)propanoic acid, 3,6-dichloro-2-pyridinecarboxylic acid, 4-amino-3,5,6-trichloro-2-pyridinecarboxylic acid, (2,4,5-trichlorophenoxy)acetic acid, 4-amino-3,5-dichloro-6-fluoro-2-pyridyloxyacetic acid, 3-amino-2,5-dichlorobenzoic acid, 3,7-dichloro-8-quinolinecarboxylic acid, and 7-chloro-3-methyl-8-quinolinecarboxylic acid.

* * * * *